(12) United States Patent
Hingston et al.

(10) Patent No.: US 9,943,394 B2
(45) Date of Patent: Apr. 17, 2018

(54) HEMOSTASIS AND CLOSURE METHODS UTILIZING MESH

(71) Applicant: Boston Scientific Scimed, Inc., Maple Grove, MN (US)

(72) Inventors: John Allen Hingston, Framingham, MA (US); Daniel Robert Quinn, Littleton, MA (US); Michael E. Zupkofska, Rockland, MA (US); Kerry L. Grant, Northbridge, MA (US); Brian Gaffney, Rutland, MA (US); Rachael Ann Rheaume, Framingham, MA (US); Kenny Joe King, Somerville, MA (US); Shawn Kerr, Millbury, MA (US); Paul Smith, Smithfield, RI (US); Michelle Fater, Worcester, MA (US); Kevin John Wilcox, Brighton, MA (US); Dylan Murphy, Walpole, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 264 days.

(21) Appl. No.: 14/625,714

(22) Filed: Feb. 19, 2015

(65) Prior Publication Data
US 2015/0238301 A1 Aug. 27, 2015

Related U.S. Application Data

(60) Provisional application No. 61/943,749, filed on Feb. 24, 2014.

(51) Int. Cl.
*A61F 2/00* (2006.01)

(52) U.S. Cl.
CPC .... *A61F 2/0063* (2013.01); *A61F 2210/0014* (2013.01); *A61F 2210/0057* (2013.01);
(Continued)

(58) Field of Classification Search
CPC ..... A61B 2210/0014; A61B 2210/0057; A61F 2220/0016; A61F 2/0063
See application file for complete search history.

(56) References Cited

U.S. PATENT DOCUMENTS

3,926,193 A * 12/1975 Hasson ............... A61B 17/085
                                                606/218
4,430,998 A *  2/1984 Harvey ............... A61B 17/085
                                                606/216
(Continued)

*Primary Examiner* — Julie A Szpira
(74) *Attorney, Agent, or Firm* — Fap Kaplun & Marcin, LLP (57) ABSTRACT

A device for causing hemostasis includes a sheet of mesh stretchable between an expanded and a retracted configuration, a size of the sheet in the retracted configuration being selected to cover a target tissue site; a spring mechanism coupled to the mesh, the spring mechanism moving between an expanded configuration and a retracted configuration when the mesh is moved between the expanded and retracted configurations; and a plurality of hooks coupled to the mesh and oriented to extend into tissue to lock the mesh in position when the mesh is placed in a desired position over the target tissue site in the expanded configuration. The hooks are lockingly engaging the target tissue so that, after the hooks have lockingly engaged the tissue, the spring mechanism reverts to the retracted configuration drawing the engaged portions of tissue radially inward.

22 Claims, 5 Drawing Sheets

(52) U.S. Cl.
CPC ................ *A61F 2220/0016* (2013.01); *A61F 2230/0006* (2013.01)

(56) References Cited

U.S. PATENT DOCUMENTS

| | | | | |
|---|---|---|---|---|
| 4,710,192 | A * | 12/1987 | Liotta | A61B 17/12 604/907 |
| 4,865,026 | A * | 9/1989 | Barrett | A61F 13/00 128/857 |
| 5,176,692 | A * | 1/1993 | Wilk | A61F 2/0063 604/103 |
| 5,234,462 | A * | 8/1993 | Pavletic | A61B 17/085 606/215 |
| 5,662,714 | A * | 9/1997 | Charvin | A61F 2/0059 606/187 |
| 6,267,772 | B1 * | 7/2001 | Mulhauser | A61F 2/0063 606/151 |
| 8,663,275 | B2 * | 3/2014 | O'Malley | A61B 17/02 606/216 |
| 8,690,960 | B2 * | 4/2014 | Hotter | A61B 17/06166 606/215 |
| 8,858,577 | B2 * | 10/2014 | Kubiak | A61B 17/1146 606/151 |
| 2005/0119694 | A1 * | 6/2005 | Jacobs | A61B 17/064 606/213 |
| 2005/0182443 | A1 * | 8/2005 | Jonn | A61B 17/085 606/213 |
| 2012/0209227 | A1 * | 8/2012 | Dunn | A61B 17/08 604/319 |
| 2015/0112290 | A1 * | 4/2015 | Dunn | A61B 17/08 604/319 |

* cited by examiner

HEMOSTASIS AND CLOSURE METHODS UTILIZING MESH

PRIORITY CLAIM

The present disclosure claims priority to U.S. Provisional Patent Application Ser. No. 61/943,749 filed Feb. 24, 2014; the disclosure of which is incorporated herewith by reference.

BACKGROUND

Pathologies of the gastro-intestinal ("GI") system, the biliary tree, the vascular system and other body lumens are commonly treated through endoscopic procedures, many of which require active and/or prophylactic hemostasis to control internal bleeding. Physicians have become increasingly willing to perform aggressive interventional and therapeutic endoscopic procedures which increase the risk of perforating the wall of the GI tract or require closure of the GI tract or wounds as part of the procedure. Many conventional devices for hemostasis are difficult may be inefficient for the type of perforation, condition or anatomy being treated.

SUMMARY OF THE INVENTION

The present disclosure relates to a device for causing hemostasis, including a device for causing hemostasis, the device comprising a sheet of mesh stretchable between an expanded and a retracted configuration, a size of the sheet in the retracted configuration being selected to cover a target tissue site. The device further comprises a spring mechanism coupled to the mesh, the spring mechanism moving between an expanded configuration and a retracted configuration when the mesh is moved between the expanded and retracted configurations. The device further comprises a plurality of hooks coupled to the mesh and oriented to extend into tissue to lock the mesh in position when the mesh is placed in a desired position over the target tissue site in the expanded configuration, the hooks lockingly engaging the target tissue so that, after the hooks have lockingly engaged the tissue, the spring mechanism reverts to the retracted configuration drawing the engaged portions of tissue radially inward.

DETAILED DESCRIPTION

The present disclosure may be further understood with reference to the following description and the appended drawings, wherein like elements are referred to with the same reference numerals. Embodiments of the disclosure are direction to a spring-loaded ring of mesh material deployable from an endoscope or other insertion instrument to cover and seal a target portion of tissue. The ring is formed of an elastic material biased to assume a substantially circular or oblong shape sized to cover a target portion of tissue. The ring is fitted with a plurality of expandable elements movable between a biased configuration having a first axial length and an expanded configuration wherein a length of the elements is increased. The expandable elements extend from respective first ends coupled to an outer border of the ring to a common second end located at a center of the ring. An inflation tube is provided on an outer periphery of the ring to move the elements between the biased and expanded configurations. Each of the expandable elements includes at least one hook permanently connected thereto in an orientation selected to engage tissue.

In an operative configuration, the ring is positioned over a target tissue site over a perforation or tear in the tissue. The inflation tube is then inflated to move the elements to the expanded configuration. The hooks are inserted into the tissue to lock the ring to the tissue. The inflation tube is then deflated to permit the element to return to the biased configuration so that the ring is radially compressed over the tissue. Specifically, the deflation causes each of the elements to move toward the common second end, causing a corresponding movement of the tissue to which the hooks are attached. Thus, movement of the device back to the biased configuration effectively seals the perforation or tear in the target tissue. The exemplary device disclosed herein provides an effective method for achieving hemostasis while minimizing the time and effort needed to perform the procedure. It should be noted that the terms "proximal" and "distal," as used herein, are intended to refer to a direct toward (proximal) and away from (distal) a user of the device.

Figure 1:
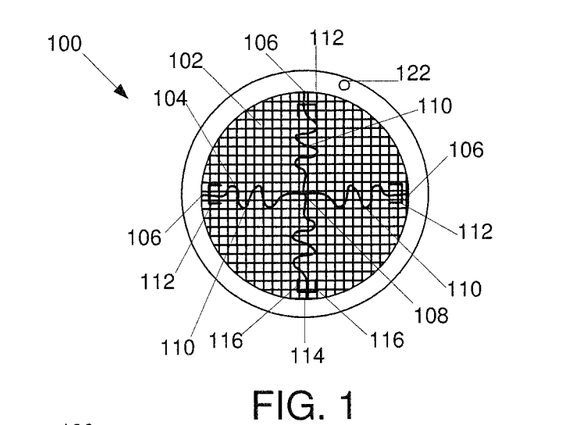
FIG. 1 shows a cross-sectional view of a hemostasis device according to an exemplary embodiment of the present invention in a first operative configuration.
Figure 2:
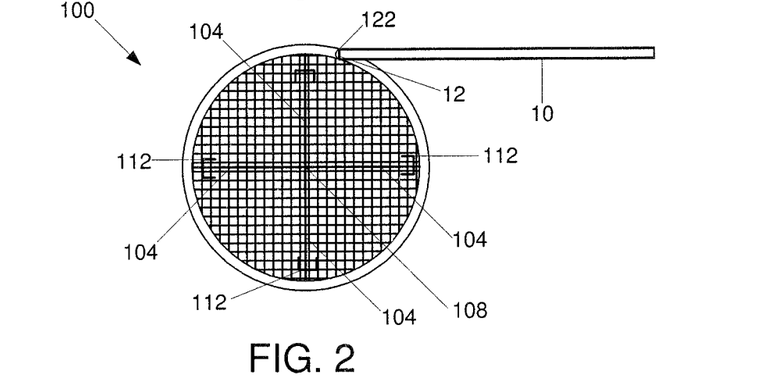
FIG. 2 shows a cross-sectional view of the hemostasis device of FIG. 1 in a second operative configuration.
Figure 3:
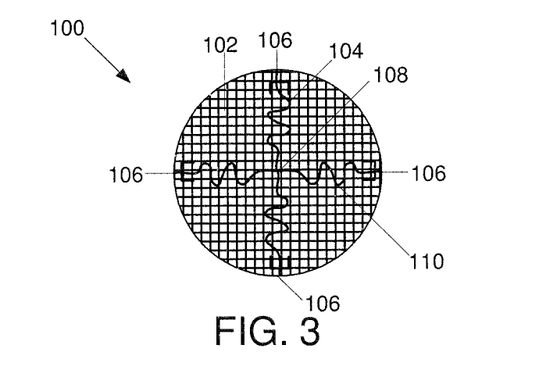
FIG. 3 shows a cross-sectional view of the hemostasis device of FIG. 1 in a third operative configuration.

As shown in FIGS. 1-3, a hemostasis device 100 according to an exemplary embodiment, includes a circular mesh element 102. It is noted, however, that any other shape of the element 102 may be used without deviating from the scope of the invention including, but not limited to, elliptical, triangular, square, rectangular and oblong. The element 102 is formed of a biocompatible mesh material. A plurality of expandable elements 104 are embedded within the element 102. The expandable elements 104 are formed of a shape-memory material (e.g., Nitinol). Each of the expandable elements 104 extends between a first end 106 coupled to an outer edge of the element 102 and a second end 108 located at a center of the element 102. The expandable elements 104 are coupled to one another at their second ends 108. In another embodiment, the expandable elements 104 may be formed as a single, unitary element. In a preferred embodiment, the element 102 includes four expandable elements 104, first ends 106 thereof being separated from one another by 90 degrees. It is noted, however, that other configurations of the expandable elements 104 are envisioned within the scope of the invention. For example, the expandable elements 104 may be positioned in any arrangement so that positions thereof are symmetric about at least one axis and preferably about at least two axes of the device 100.

The expandable elements 104 are formed as elongated filaments of a shape-memory material, each having a spring portion 110 positioned along at least a portion thereof. The spring portion 110 of a first one of the expandable elements 104 follows a curved path having one or more curvatures therein selected to reduce an axial length of the element 104.

As will be described in greater detail later on, this expandable element 104 is movable between a first configuration toward which it is biased in which a plurality of curves are formed therein, as shown in FIG. 1, and an axially expanded configuration in which the expandable element 104 is straight and extends along a single axis. In another embodiment, any of all of the expandable elements 104 may include a smaller number or degree of curvatures in the expanded configuration. That is, the element 104 may still include some curvature in the expanded configuration as long as an axial length thereof between the first and second ends 106, 108 is increased with respect to a length thereof in the biased configuration.

Figure 4:
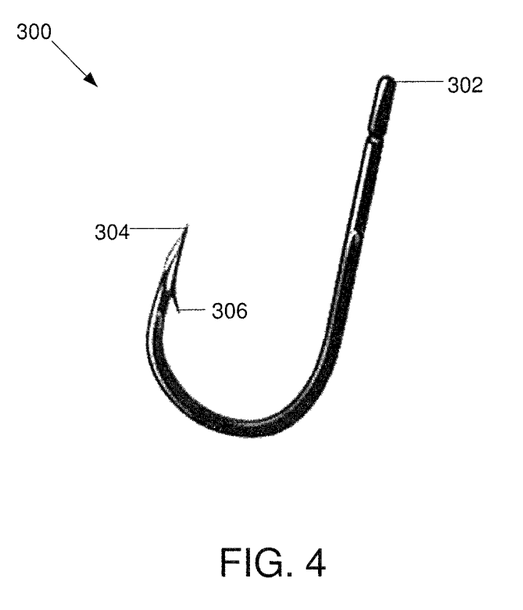
FIG. 4 depicts an alternate embodiment of a tissue-grasping hook.

One or more hooks 112 are provided on each of the expandable elements 104. The hooks 112 are mounted on the expandable elements 104 radially outward from the springs 110 at portions of the expandable elements 104 the shape of which remains substantially the during movement of the expandable elements 104 between the biased and expanded configuration. Each of the hooks 112 includes a body 114 having first and second arms 116 at free ends thereof. The arms 116 are formed to extend into a target portion of tissue in an operative configuration. The body 114 of each hook 112 is bonded to a corresponding one of the expandable elements 104 in a fixed position so that, when the mesh element 102 is positioned over target tissue, the hook 112 faces the target tissue. The hooks 112 may be formed, for example, of the same shape-memory material as the expandable elements 104. In one embodiment, the hooks 112 and elements 104 may be a unibody structure. The hooks 112 are formed with a shape formed to lockingly engage tissue when pushed thereinto. In one embodiment, the hooks 112 have a greater width at the body 114 and a reduced width at free ends of the arms 116. As those skilled in the art will understand, this shape prevents the hooks 112 from being removed from the tissue when pushed thereinto. In another embodiment, as shown in FIG. 4, a hook 300 extends from a first end 302 permanently coupled to the mesh element 102 and follows a curved shape to a second end 304, which includes a sharpened tissue-penetrating tip. A barb 306 is provided on an inner surface of the hook 300 to prevent the hook 300 from being removed from the tissue once inserted therein. Specifically, the barb 306 is oriented in a direction opposite the second end 304 to prevent withdrawal thereof from the tissue.

The mesh element 102 is removably coupled to an inflation tube 120 during insertion to a target tissue site. In one embodiment, the inflation tube 120 is permanently attached to an outer border of the element 102. In another embodiment, the inflation tube 120 is placed around the element 102 prior to insertion through a working channel of an endoscope (not shown) or other insertion device. The mesh element 102 and the inflation tube 120 are then advanced through the insertion device to the target site and, the tube 120 may be inflated to move the mesh element 102 and the expandable elements 104 to the expanded configuration for implantation on the target tissue. After this implantation has been completed as will be described below, the inflation tube 120 may be separated from the mesh element 102 and removed from the body. Specifically, the tube 120 may be coupled to the element 102 by an adhesive or knotted filament (e.g., thread, wire). Upon inflation of the inflation tube 120 in situ, the inflation tube 120 is automatically dislodged from the element 102, allowing removal thereof from the body. The inflation tube 120 includes an inflation port 122 on an outer surface thereof permitting inflation and deflation of the inflation tube 120 as desired. The inflation tube 120 is formed of a biocompatible highly compliant material that remains substantially pliable regardless of a pressure within the tube 120, as those skilled in the art will understand.

In accordance with an exemplary method according to the invention, the mesh element 102 may be fitted with the inflation tube 120 in a pre-implantation step (e.g., during manufacturing). The device 100 is then inserted through the working channel of the endoscope (not shown) or other insertion device in the biased configuration as shown in FIG. 1. The device 100 may be folded, wrapped or crimped during insertion to permit insertion through the working channel. In another embodiment, the device 100 may be sized to permit insertion thereof through the working channel without folding. The device 100 is then advanced out of a distal end of the endoscope and placed over a target tissue site. An inflation device 10 is then advanced through the endoscope so that a distal end 12 thereof is coupled to the inflation port 122. In another embodiment, the inflation device 10 may be coupled to the inflation port 122 prior to insertion thereof through the endoscope. Positive pressure is then applied through the inflation device 10 to inflate the inflation tube 120, as shown in FIG. 2. The inflation causes the expandable elements 104 to straighten, moving to the expanded configuration and increasing an axial length of the expandable elements 104.

Once the device 100 has been moved to the expanded configuration, as can be confirmed via observation through an observation channel of the endoscope, the hooks 112 are forced into the tissue. Specifically, a separate tool (not shown) may be inserted through the endoscope and to exert a force on the hooks 112 moving the hooks into the tissue at the target site. Once the hooks have been locked to the tissue, negative pressure is applied through the inflation device 10 to deflate the inflation tube 102, removing an expansive pressure applied to the expandable elements 104 and permitting the elements 104 to return to their original biased configuration. As the axial length of the expandable elements 104 is reduced, the hooks 112 are moved radially inward toward the second ends 108 of the expandable elements 104 drawing the tissue to which the hooks 112 are connected radially inward as well. Thus, separated portions of tissue may be drawn together sealing of a perforation or wound in the tissue. The inflation device 10 is then removed from the body.

For embodiments in which the tube 120 is removably coupled to the element 102, an exemplary method is substantially to the method described above, except as follows. Once the element 102 is positioned over the target tissue, the tube 120 is inflated to a first configuration so that a pressure within the tube 120 is at a first value. In the first configuration, an axial length of the elements is increased, as shown in FIG. 2. The hooks 112 are then forced into the tissue in the same manner disclosed above. Once the hooks 112 are locked to the tissue, the tube 120 is further inflated so that a pressure therein is greater than the first pressure and at least greater than a threshold value sufficient to cause the coupling between the tube 120 and element 102 to separate. Once this value has been met or exceeded, the tube 120 separates from the element 102, the separating permitting the elements 104 to return to the biased configuration, as shown in FIG. 3. The inflation tube 120 and inflation device 10 may then be removed from the body. In one embodiment, the inflation tube 120 may be deflated prior to removal to permit insertion thereof through the working channel of the endoscope.

FIG. 4 depicts a hemostasis device 200 according to another embodiment of the invention. The device 200 is substantially similar to the device 100 except as noted below. The hemostasis device 200 comprises a bioabsorbable mesh 204 embedded with one or more springs 206. In one embodiment, a plurality of springs 206 extend across the device 200 along parallel longitudinal axes 208. In an operative configuration, the longitudinal axes 208 extend parallel to a desired compression axis 210, as will be described in greater detail hereinafter. The springs 206 are embedded in the mesh 204. Specifically, the wire of the springs 206 may be woven through the mesh 204. In another embodiment, the springs 206 may be positioned between two layers of the mesh 204, which are subsequently sewn together. Free ends 212, 214 of the springs 206 are permanently attached to the mesh 204 to maintain the position of the springs 206 thereon and to impart a desired flexibility to the mesh 204 as the spring 206 is stretched and/or compressed. The spring 206 is attached to the mesh in a first stretched configuration so that adjacent turns of the coiled spring 206 are separated from one another by a first non-zero distance. In an exemplary embodiment, the mesh 204 is sufficiently rigid to maintain the spring 206 in the expanded configuration without buckling or folding.

Figure 5:
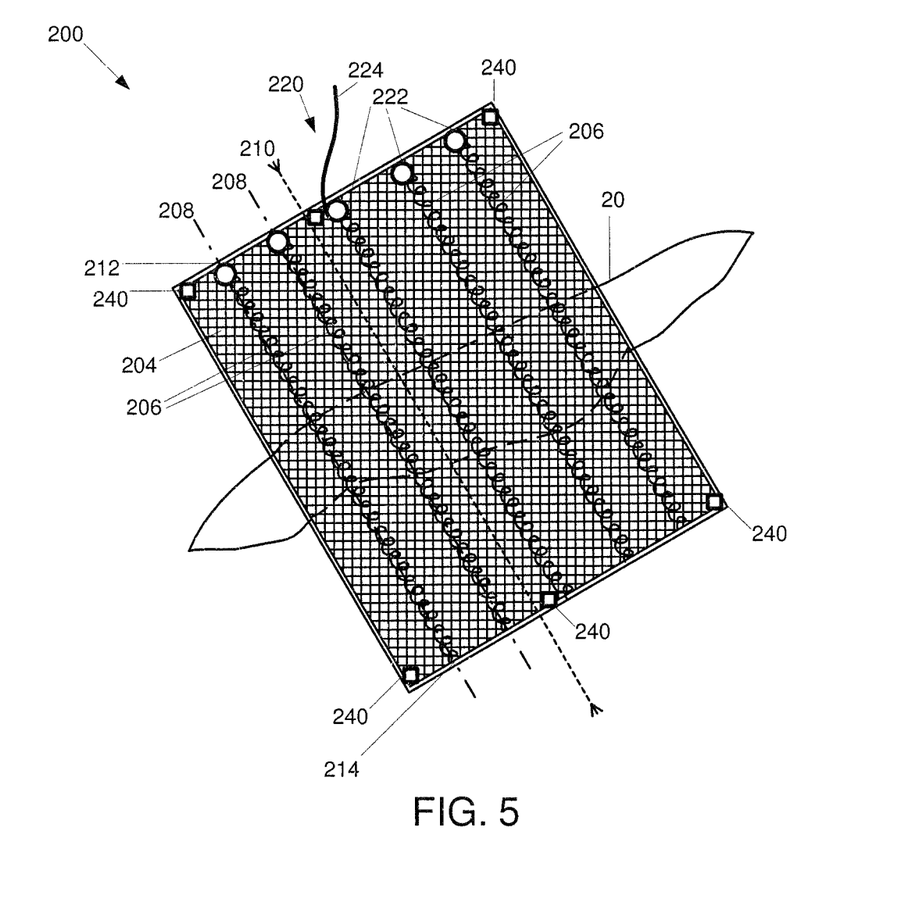
FIG. 5 shows top view of a hemostasis device according to an alternate embodiment of the invention.

The mesh 204 also includes a plurality of hooks 240 formed to penetrate tissue at the target site. The hooks 240 may be formed substantially similarly to the hooks 112 and may be inserted into the tissue in substantially the same manner. In another embodiment, the mesh 204 may be secured to the tissue via any of hemostatic clips such as resolution clips, barbs, sutures, t-tags, adhesive, etc. It is noted that these attachment mechanisms are exemplary only and that any other attachment mechanism may be used without deviating from the scope of the disclosure. Furthermore, it is noted that the placement of the hooks 240 depicted in FIG. 5 is exemplary only and that any other number and placement may be used without deviating from the scope of the disclosure.

Figure 6:
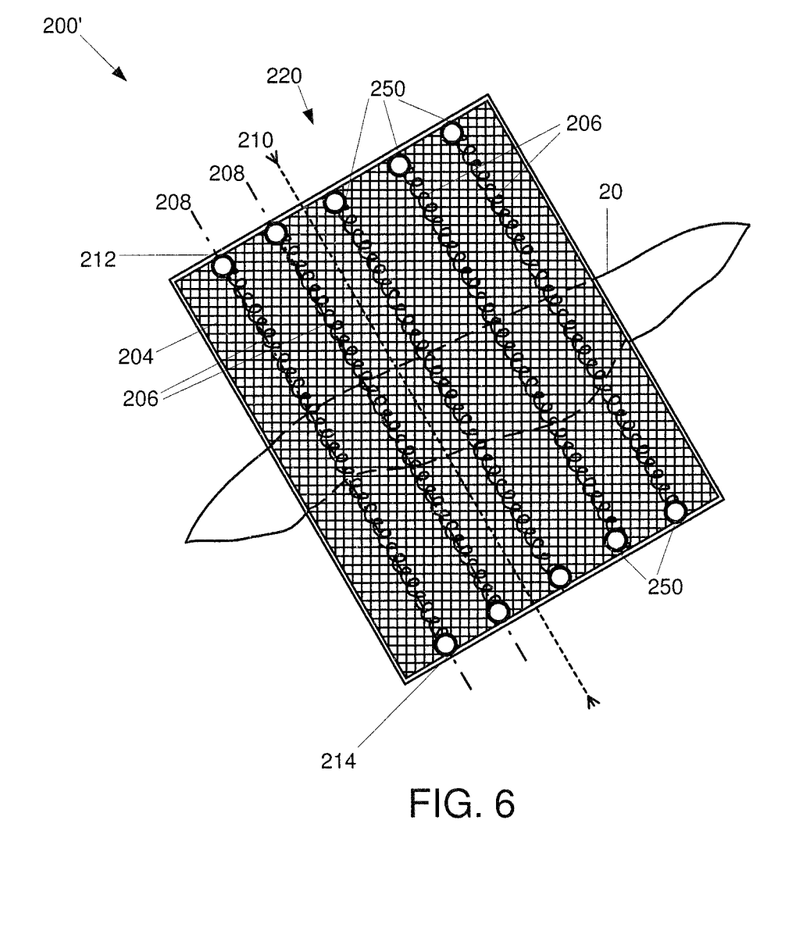
FIG. 6 shows top view of a hemostasis device according to another alternate embodiment of the invention.
Figure 7:
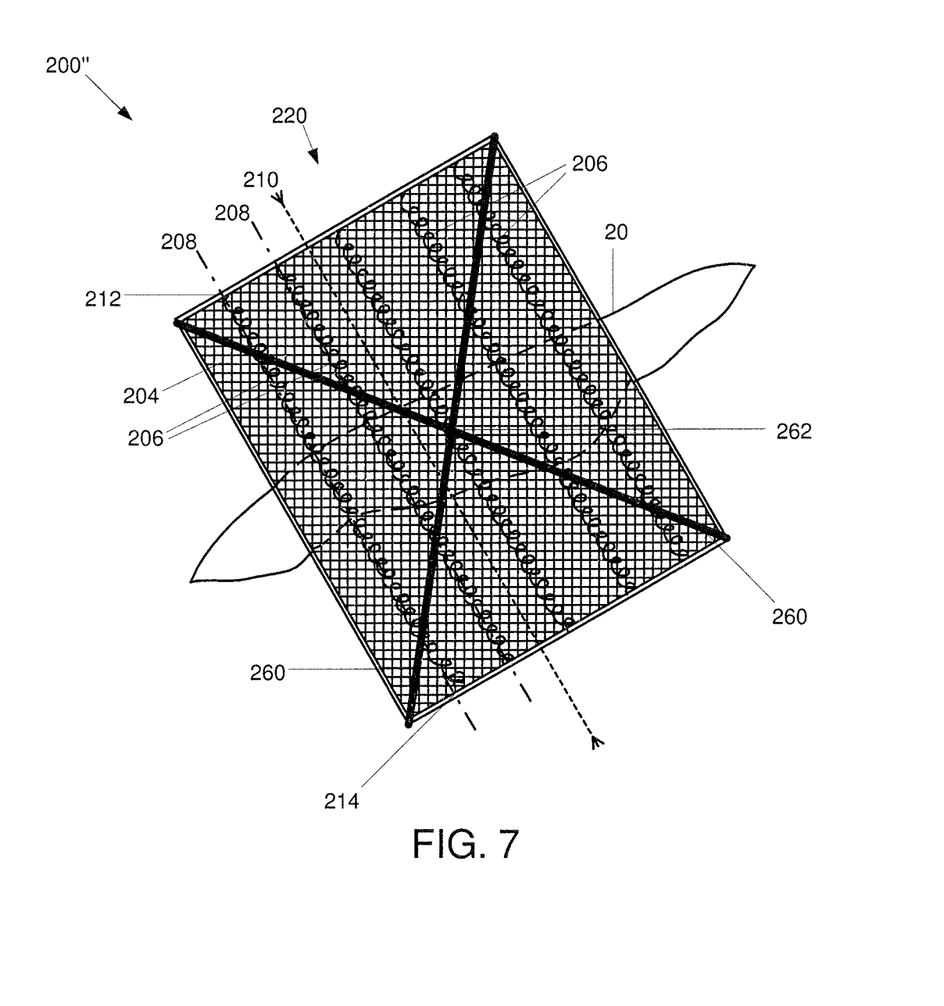
FIG. 7 shows top view of a hemostasis device according to another alternate embodiment of the invention.

The device 200 further comprises one or more mechanical triggers 220 each freeing one or more of the springs 206 to contract from the expanded configuration shown in FIG. 4 to a compressed configuration. In the compressed configuration, the springs 208 are compressed along the axis 208 reducing an axial length thereof. In one embodiment, adjacent turns of the coiled springs 206 contact one another in the compressed configuration. In another embodiment, the adjacent turns may be separated from one another by a second distance smaller than the first distance. In one embodiment, the mechanical triggers 220 may be formed as knotted threads or filaments 222 at one or both ends of each of the springs 208. Each knotted thread 222 may be coupled to one or more of the springs 208 to couple the springs 208 to the mesh. The mesh may then be expanded over the tissue and secured thereto via hooks 240 to retain the spring 208 in the expanded configuration of FIG. 4 over the tissue. The knotted thread 222 may be coupled to a pull-string 224 extending therefrom and having a length selected to facilitate grasping thereof. In an operative configuration, a surgeon or other user pulls the pull-string 224 to disengage the knotted thread 222 from the spring(s) 208 to which it is coupled, permitting the spring(s) 208 to retract to the compressed configuration. In one embodiment, a pull-string 224 may be connected to a knotted thread 222 on each of the springs 208 so that retraction of the pull-string frees all of the springs 206 to simultaneously retract to the compressed configuration. In another embodiment, a separate knotted thread 222 is attached to end of each of the springs 206 with each of the knotted threads 222 including a separate pull-string 224 so that a user may individually free the springs 206 to retract to the compressed configuration. In yet another embodiment, as shown in FIG. 6, a device 200' may be formed so that ends of the springs 206 are connected to the mesh 204 via connection 250. The connections 250 are oriented on a tissue-facing side of the mesh 204 and are formed of a biodegradable material which degrades under contact with the tissue. In a preferred embodiment, the connection 250 is formed of a material selected and has a size selected to permit degradation thereof over a predetermined time period after coming into contact with the tissue (e.g., a number of seconds, one or more minutes, etc.). Upon degradation of the connection 250, the springs 206 are freed to move from the axially expanded configuration to a compressed configuration to close the perforation, as will be described in greater detail with respect to the exemplary method below. In yet another embodiment, as depicted in FIG. 7, a device 200" may include two or more wires 260 positioned over the mesh 204, the wires 260 being substantially rigid to maintain the springs 206 in the expanded configuration. The wires 260 may extend from opposing corners of the mesh 204 to intersect at a point 262. The wires 260 may be attached to the mesh 204 using a known attachment means. In one embodiment, the wires 260 may be embedded within the mesh 204. In an operative configuration, once the mesh 204 has been secured to a target portion of tissue, a user may cut the wires at the point 262 to release the tension maintaining the springs 206 in the expanded configuration. The springs 206 then contract over the tissue to close the perforation. The cut wires 260 may remain embedded within the mesh 204 or, in another embodiment, may be removed therefrom using any appropriate tool. In another embodiment, the wires 260 may be coupled to one another and the mesh 204 by a string (not shown). In an operative configuration, the user may cut, un-knot or otherwise remove the string to remove the wire from the mesh, thereby release the expansive pressure applied by the wires 260 to the mesh and permitting the springs 206 to contract.

The device 200 is advanced through a working channel of an endoscope (not shown) or other insertion device to a target site in the body. The device 200 may be folded or otherwise compressed to permit insertion thereof through the working channel. The device 200 is then advanced out of a distal opening of the working channel and positioned over a target tissue site 20. The mesh 204 may be positioned so that a target tear or perforation 22 to be closed is located at an approximate center of the mesh 204. Due to the tension created by the coupling of ends 212, 214 of the springs 206 to the mesh 204, the device 200 springs to a substantially flat, expanded configuration upon being released from the endoscope. The device 200 may then be manipulated so that longitudinal axes 208 of the springs 206 are aligned with a desired compression axis 210 (i.e., an axis corresponding to a direction in which tissue is to be axially moved). Once in the desired position and orientation, hooks 240 are used to secure the mesh 204 to the tissue. In a next step, one or more mechanical triggers 220 may be released by applying a predetermined force to the pull-tab 224 sufficient to break or unravel the knotted thread 220. Actuation of the mechanical trigger 220 removes a force holding the springs 206 in the expanded configuration. Ends 212, 214 of the springs 206 are then free to retract to a compressed configuration, causing a corresponding compression of the mesh 204. As the ends 212, 214 move toward one another, the hooks 240 cause a corresponding compression of the tissue, thereby closing the tear or perforation 22 in the tissue 20. In one embodiment, as the springs 206 are compressed, tissue located below the springs is drawn into the spaces between adjacent turns of the coiled springs 206. Thus, as the ends 212, 214 move toward one another, the springs 206 draw the tissue below the springs 206 together along the compression axis, thereby closing the tear or perforation 22 in the tissue 20.

It will be understood by those of skill in the art that individual features of the embodiments described above may be omitted and or combined to form alternate embodiments. Furthermore, it will be understood by those skilled in the art that various modifications can be made in the structure and the methodology of the present invention, without departing from the spirit or scope of the present disclosure. Thus, it is intended that the present disclosure cover any and all modifications and variations.

What is claimed is:

1. A medical device, comprising:
   a sheet of mesh stretchable between an expanded and a retracted configuration, a size of the sheet in the retracted configuration being selected to cover a target tissue site;
   a spring mechanism coupled to the mesh, the spring mechanism moving between an expanded configuration and a retracted configuration when the mesh is moved between the expanded and retracted configurations; and
   a plurality of hooks directly coupled to the spring mechanism and oriented to extend into a target tissue to lock the mesh in position when the mesh is placed in a desired position over the target tissue site in the expanded configuration, the hooks configured to lockingly engage the target tissue so that, after the hooks have lockingly engaged the tissue, the spring mechanism reverts to the retracted configuration drawing the engaged portions of tissue radially inward.

2. The device of claim 1, wherein the mesh is one of circular and oblong and is sized to cover a target portion of tissue.

3. The device of claim 1, wherein the spring mechanism includes a plurality of expandable elements, each of the expandable elements extending from a first end coupled to a radially outer portion of the mesh to a second end at a center of the mesh.

4. The device of claim 3, wherein a first pair of the expandable elements are axially aligned with one another and a second pair of the expandable elements are axially aligned with one another, the first pair extending orthogonal to the second pair.

5. The device of claim 1, wherein the spring mechanism is formed of a shape-memory material.

6. The device of claim 3, wherein, in the retracted configuration, the first and second expandable elements extend along a curved path.

7. The device of claim 6, wherein, in the expanded configuration, the plurality of expandable elements are straighter than in the retracted configuration.

8. The device of claim 3, further comprising an inflation tube extending around an edge of the mesh, the inflation tube including an inflation port permitting inflation thereof, inflation of the inflation tube maintaining the mesh and the expandable elements in the expanded configuration.

9. The device of claim 1, wherein the spring mechanism includes a plurality of coils secured to the mesh parallel to one another so that the mesh and the expandable elements retract linearly from the expanded configuration to the retracted configuration.

10. The device of claim 9, further comprising a trigger mechanism coupled to the mesh to move the spring mechanism between the expanded configuration and the retracted configuration.

11. The device of claim 10, wherein the trigger mechanism is one of a knot and pull-tie, biodegradable connection and releasable rigid wire.

12. The device of claim 1, wherein the target tissue is within a living body.

13. The device of claim 1, wherein the device is sufficiently flexible to be folded into an insertion configuration permitting the device to be inserted through a working channel of a flexible endoscope.

14. A system for causing hemostasis, comprising:
    a sheet of mesh stretchable between an expanded and a retracted configuration, a size of the sheet in the retracted configuration being selected to cover a target tissue site;
    a spring mechanism coupled to the mesh, the spring mechanism moving between an expanded configuration and a retracted configuration when the mesh is moved between the expanded and retracted configurations;
    plurality of hooks directly coupled to the spring mechanism and oriented to extend into tissue to lock the mesh in position when the mesh is placed in a desired position over the target tissue site in the expanded configuration, the hooks configured to lockingly engage the target tissue so that, after the hooks have lockingly engaged the tissue, the spring mechanism reverts to the retracted configuration drawing the engaged portions of tissue radially inward; and
    a trigger mechanism operable to move the spring mechanism between the expanded and retracted configurations.

15. The system of claim 14, wherein the spring mechanism includes a plurality of expandable elements, each of the expandable elements extending from a first end coupled to a radially outer portion of the mesh to a second end at a center of the mesh.

16. The system of claim 15, wherein a first pair of the expandable elements are axially aligned with one another and a second pair of the expandable elements are axially aligned with one another, the first pair extending orthogonal to the second pair.

17. The system of claim 14, wherein spring mechanism is formed of a shape-memory material.

18. The system of claim 14, wherein the trigger mechanism includes an inflation tube extending around an edge of the mesh, the inflation tube including an inflation port permitting inflation thereof, inflation of the inflation tube maintaining the mesh and the expandable elements in the expanded configuration and deflation of the inflation tube moving the spring mechanism to the retracted configuration.

19. The system of claim 14, wherein the spring mechanism includes a plurality of coils secured to the mesh parallel to one another so that the mesh and the expandable elements retract linearly from the expanded configuration to the retracted configuration.

20. The system of claim 19, wherein the trigger mechanism is one of a knot and pull-tie, biodegradable connection and releasable rigid wire.

21. A method for causing hemostasis, comprising:
    positioning a sheet of mesh over a target portion of tissue, the mesh being stretchable between an expanded and a retracted configuration, the mesh including a spring mechanism coupled to the mesh;

anchoring the mesh in the expanded configuration over the tissue via plurality of hooks directly coupled to the spring mechanism to lock the mesh in position over the target tissue site in the expanded configuration; and actuating a trigger mechanism to move the spring mechanism from the expanded configuration to the retracted configuration, the movement causing the mesh to move from the expanded configuration to the retracted configuration, bringing opposing ends of the tissue toward another to close or seal the target tissue.

22. The method of claim 21, further comprising:

inflating an inflation tube coupled to an outer periphery of the mesh to move the mesh to the expanded configuration prior to anchoring; and deflating the inflation tube to move the anchored mesh to the retracted configuration over the tissue.

* * * * *